(12) United States Patent
Thibodeau

(10) Patent No.: US 10,195,123 B2
(45) Date of Patent: Feb. 5, 2019

(54) EMULSIFIERS HAVING WATER-IN-OIL-STABILIZING PROPERTIES AND COMPOSITIONS, USES AND METHODS RELATING TO SAME

(71) Applicant: Innovacos Corp., Mt. Arlington, NJ (US)

(72) Inventor: Alain Thibodeau, Québec (CA)

(73) Assignee: Innovacos Corp., Mt. Arlington, NJ (US)

( * ) Notice: Subject to any disclaimer, the term of this patent is extended or adjusted under 35 U.S.C. 154(b) by 0 days.

(21) Appl. No.: 15/305,018

(22) PCT Filed: Apr. 22, 2015

(86) PCT No.: PCT/CA2015/050335
§ 371 (c)(1),
(2) Date: Oct. 18, 2016

(87) PCT Pub. No.: WO2015/161378
PCT Pub. Date: Oct. 29, 2015

(65) Prior Publication Data
US 2017/0172859 A1    Jun. 22, 2017

Related U.S. Application Data

(60) Provisional application No. 61/982,412, filed on Apr. 22, 2014.

(51) Int. Cl.
| | |
|---|---|
| *A61K 8/06* | (2006.01) |
| *A61K 47/12* | (2006.01) |
| *A61K 47/32* | (2006.01) |
| *A61K 47/34* | (2017.01) |
| *A61K 9/107* | (2006.01) |
| *A61K 8/365* | (2006.01) |
| *A61K 8/39* | (2006.01) |
| *A61Q 19/00* | (2006.01) |
| *A61K 8/85* | (2006.01) |
| *B01F 17/00* | (2006.01) |
| *A61K 8/37* | (2006.01) |
| *A61K 8/58* | (2006.01) |
| *A61K 8/84* | (2006.01) |
| *A61K 47/14* | (2017.01) |
| *A61K 47/24* | (2006.01) |
| *A61Q 17/04* | (2006.01) |

(52) U.S. Cl.
CPC .............. *A61K 8/064* (2013.01); *A61K 8/365* (2013.01); *A61K 8/37* (2013.01); *A61K 8/39* (2013.01); *A61K 8/585* (2013.01); *A61K 8/84* (2013.01); *A61K 8/85* (2013.01); *A61K 9/107* (2013.01); *A61K 47/12* (2013.01); *A61K 47/14* (2013.01); *A61K 47/24* (2013.01); *A61K 47/32* (2013.01); *A61K 47/34* (2013.01); *A61Q 17/04* (2013.01); *A61Q 19/00* (2013.01); *B01F 17/0028* (2013.01); *A61K 2800/10* (2013.01); *A61K 2800/30* (2013.01); *A61K 2800/52* (2013.01)

(58) Field of Classification Search
None
See application file for complete search history.

(56) References Cited

U.S. PATENT DOCUMENTS

2007/0166270 A1* 7/2007 Neuss .................. A61K 8/8152
424/70.31

FOREIGN PATENT DOCUMENTS

| | | |
|---|---|---|
| CA | 2469174 A1 | 1/2005 |
| DE | 102006033845 A1 | 1/2008 |
| WO | 9904749 A2 | 2/1999 |

OTHER PUBLICATIONS

DE102006033845 translation retrieved from Espacenet on Aug. 16, 2017.*
International Search Report and Written Opinion for Application No. PCT/CA2015/050335 dated Jul. 17, 2015.
International Preliminary Report on Patentability issued PCT/CA2015/050335 dated Nov. 3, 2016.

* cited by examiner

*Primary Examiner* — Jessica Worsham
(74) *Attorney, Agent, or Firm* — Lerner, David, Littenberg, Krumholz & Mentlik, LLP

(57) ABSTRACT

Emulsifiers are provided that are able to stabilize water-in-oil emulsions. The emulsifiers are homogenous and have a relatively low melting point (e.g., soft pastes, gels or liquids at room temperature), enabling their use in cold-process methods/formulations which reduce energy consumption, manufacturing costs, as well as allow the use thermolabile active ingredients. The water-in-oil emulsifiers may comprise: (a) polyglycerol fatty acid esters consisting of saturated and unsaturated fatty acid esters of polyglycerol; (b) polyhydroxystearic acid copolymers consisting of copolymers of hydroxystearic acid with saturated and unsaturated fatty acids; and (c) hydroxystearic acid. Methods and uses relating to the emulsifiers are also described, for example in cosmetic and pharmaceutical compositions.

43 Claims, No Drawings

EMULSIFIERS HAVING WATER-IN-OIL-STABILIZING PROPERTIES AND COMPOSITIONS, USES AND METHODS RELATING TO SAME

CROSS-REFERENCE TO RELATED APPLICATIONS

The present application is a national phase entry under 35 U.S.C. § 371 of International Application No. PCT/CA2015/050335, filed Apr. 22, 2015, published in English, which claims priority from U.S. provisional patent application Ser. No. 61/982,412, filed on Apr. 22, 2014, the disclosures of which are incorporated herein by reference in their entirety.

FIELD OF THE INVENTION

The present invention relates to emulsifiers having water-in-oil-stabilizing properties and compositions, uses and methods relating to same. More specifically, the present invention relates to water-in-oil-stabilizing emulsifiers comprising: (a) saturated and unsaturated fatty acid esters of polyglycerol; (b) copolymers of hydroxystearic acid with saturated and unsaturated fatty acids; and (c) hydroxystearic acid.

BACKGROUND OF THE INVENTION

An emulsion consists of two immiscible liquids mixed together with small droplets of one liquid dispersed in the other liquid. The dispersion is usually not stable and all the droplets "clump" together over time to form two layers or phases. An emulsifier is a substance that can stabilize an emulsion by increasing its kinetic stability, for example, by inhibiting droplet coalescence (i.e., preventing the droplets from clumping together). The majority of emulsions can be classified according to the chemical nature of the liquids, such as oil-in-water (O/W) or water-in-oil (W/O).

W/O emulsions are desirable in many industries (e.g., the cosmetics industry), yet many more emulsifiers exist that can stabilize O/W emulsions than W/O emulsions. Producing a stable W/O emulsion represents a challenge and only a few emulsifiers currently exist that can, by themselves (i.e., acting as a primary emulsifier), adequately stabilize such an emulsion. Furthermore, W/O emulsions comprising polar oils are particularly difficult to stabilize due to their amphiphilic nature. Thus, relatively few emulsifiers that can stabilize W/O systems have been described.

Esters can be synthesized from compounds such as vegetables fatty acids, fatty alcohols, and polyalcohols. The use of saturated fatty acids in esterification reactions can be advantageous, since they can produce stable and homogeneous esters (e.g., in the form of high melting point waxes or limpid liquids), without the formation of a liquid/solid heterogeneous phase. However, the use of unsaturated fatty acids in uncontrolled esterification reactions can lead to the formation of non-homogeneous products such as the formation of precipitates and the simultaneous presence of liquid and solid phases, which are often not desirable (e.g., for cosmetic emulsions).

Such problems are often caused by the presence of molecules having very different melting points. For example, saturated fatty acids (e.g., C18 fatty acids) exist as solids at room temperature, while unsaturated fatty acids (e.g., C18:1 fatty acids) exist as liquids at room temperature. Using non-homogeneous emulsifying compositions may lead to undesirable effects such as formulation instability, reduction of sensorial properties, and lack of efficacy. When dealing with such products with very different melting points, it can become necessary to use warm rooms or mechanical mixing procedures to homogenize the products before they can be used.

In some cases, the melting point of a raw material can be an important factor to consider. Solid compositions (e.g., waxes) require heat to be melted before they can be homogenized or emulsified with other ingredients. The use of elevated temperatures during processes/formulations required to pre-melt raw materials not only increases energy consumption (and thus manufacturing costs), but can also be problematic when working with thermolabile active ingredients.

Accordingly, there exists a need for novel emulsifiers, including emulsifiers capable of adequately stabilizing W/O emulsions that address at least some of the above mentioned problems.

The present description refers to a number of documents, the content of which is herein incorporated by reference in their entirety.

SUMMARY OF THE INVENTION

The present invention relates to the discovery of emulsifiers with advantageous properties that are able to stabilize water-in-oil emulsions. In some embodiments, the emulsifiers are homogenous and have a relatively low melting point, enabling their use in cold-process methods/formulations, which reduce energy consumption, manufacturing costs, as well as allow the use of thermolabile active ingredients. The advantages of emulsifiers of the present invention stem from synergistic interactions between their principal components.

In some aspects, the present invention relates to a W/O-stabilizing emulsifier comprising: (a) polyglycerol fatty acid esters comprising saturated and unsaturated fatty acid esters of polyglycerol; (b) polyhydroxystearic acid copolymers comprising copolymers of hydroxystearic acid with saturated and unsaturated fatty acids; and (c) hydroxystearic acid.

In some aspects, the present invention relates to a W/O-stabilizing emulsifier comprising: (a) polyglycerol fatty acid esters consisting of saturated and unsaturated fatty acid esters of polyglycerol; (b) polyhydroxystearic acid copolymers consisting of copolymers of hydroxystearic acid with saturated and unsaturated fatty acids; and (c) hydroxystearic acid.

In some embodiments, (a) consists of mono-substituted or mono-esterified polyglycerol fatty acid esters. In embodiments, (a) consists of saturated and unsaturated fatty acid esters of polyglycerol-n, wherein n is an integer from 2 to 10 (e.g., n is 2, 3, 4, 6 or 10). In some embodiments, n is 2.

In some embodiments, (b) consists of copolymers of hydroxystearic acids mono-substituted or mono-esterified with fatty acids. In some embodiments, (b) consists of copolymers of 12-hydroxystearic acid with saturated and unsaturated fatty acids. In some embodiments, (b) consists of copolymers of about 0.5 to 0.8 equivalents of 12-hydroxystearic acid with about 1 equivalent of saturated and unsaturated fatty acids. In some embodiments, (b) consists of copolymers of about 0.6 equivalents of 12-hydroxystearic acid with about 1 equivalent of saturated and unsaturated fatty acids. In some embodiments, (b) has an acid value of between about 145 mg KOH/g and about 165 mg KOH/g. In some embodiments, (b) has an acid value of about 155 mg KOH/g.

In some embodiments, (c) consists of 12-hydroxystrearic acid.

In some embodiments, (a), (b), or both (a) and (b) are produced from a mixture of saturated and unsaturated fatty acids comprising: (i) 10-20% w/w palmitic acid (C16); (ii) 0.2-5% w/w palmitoleic acid (C16:1); (iii) 10-20% w/w stearic acid (C18); (iv) 40-60% w/w oleic acid (C18:1); (v) 10-20% w/w linoleic acid (C18:2); and (vi) 0.3-5% w/w linolenic acid (C18:3). In some embodiments, the mixture of saturated and unsaturated fatty acids is from: almond oil, olive oil, coconut oil, cocoa tree oil, soybean oil, palm oil, sunflower oil, or any combination thereof (i.e. any combination of at least 2 of these oils, or of at least 3, at least 4, at least 5, at least 6 or all 7 of these oils) (e.g., a combination of olive oil, coconut oil, cocoa tree oil, soybean oil and sunflower oil).

In some embodiments, (a), (b) and/or (c) are obtained from natural sources. In some embodiments, (a), (b) and/or (c) are obtained from plant sources. In some embodiments, (a), (b) and/or (c) are obtained from vegetable sources.

In some embodiments, the above mentioned emulsifier has a melting point suitable for cold-process emulsions. In some embodiments, the melting point is below about 48, 47, 46, 45, 44, 43, 42, 41, 40, 39, 38, 37, 36, 35, 34, 33, 32, 31, 30, 29, 28, 27, 26, 25, 24, 23, 22, or 21° C. In some embodiments, the melting point is between about 19° C. and about 48° C.

In some embodiments, the emulsifier comprises: (a) about 35-52% w/w of the polyglycerol fatty acid esters; (b) about 40-65% w/w of the polyhydroxystearic acid copolymers; and (c) about 0.5-6% w/w of the hydroxystearic acid.

In some embodiments, the emulsifier has a viscosity of between about 2000 cP to about 150,000 cP, more specifically about 3000 cP to about 110,000 cP at 25° C. In some embodiments, the emulsifier is homogenous at room temperature. In some embodiments, the emulsifier enables stabilization of a W/O emulsion comprising up to 90%, up to 91%, up to 92%, up to 93%, or up to 94% w/w water for at least 1 month at 50° C. In some embodiments, the emulsifier enables stabilization of a W/O emulsion comprising a polar oil (e.g., vegetable oils such as olive oil, jojoba oil, germ oil, and almond oil).

In some aspects, the present invention relates to a composition comprising water-in-oil (W/O) emulsion stabilized by the emulsifier as defined above. In some embodiments, the composition further comprises a thermolabile active ingredient. In some embodiments, the composition further comprises an emollient. In some embodiments, the composition further comprises a thickener or rheological modifier.

In some embodiments, the composition comprises up to about 90%, up to about 91%, up to about 92%, up to about 93%, up to about 93.5% or up to about 94% w/w water. In some embodiments, the composition comprises a W/O emulsion is stable for at least 1 month at 50° C.

In some embodiments, the composition is a cosmetic or a pharmaceutical composition. In some embodiments, the composition is a dermatological composition. In some embodiments, the composition is a liquid, cream, gel, or wax.

In some embodiments, the composition further comprises silicon oil, such as a cyclosiloxane (e.g., cyclopentasiloxane and/or cyclohexasiloxane).

In some embodiments, the composition further comprises a silicon emulsifier.

In some embodiments, the composition is free of paraffin.

In some aspects, the present invention relates to a method for producing a water-in-oil (W/O)-stabilizing emulsifier, the method comprising mixing: (a) saturated and unsaturated fatty acid esters of polyglycerol produced by esterifying a mixture of saturated and unsaturated fatty acids with polyglycerol; (b) copolymers of hydroxystearic acid with saturated and unsaturated fatty acids produced by esterifying a mixture of saturated and unsaturated fatty acids with hydroxystearic acid; and (c) hydroxystearic acid, thereby producing the water-in-oil (W/O)-stabilizing emulsifier. In some embodiments, (a) consists of mono-substituted or mono-esterified polyglycerol fatty acid esters. In some embodiments, (a) is produced by esterifying a mixture of saturated and unsaturated fatty acids with polyglycerol-n, wherein n is an integer from 2 to 10. In some embodiments, n is 2, 3, 4, 6 or 10. In some embodiments, n is 2.

In some embodiments, (b) consists of hydroxystearic acid mono-substituted or mono-esterified with fatty acids. In some embodiments, (b) is produced by esterifying a mixture of saturated and unsaturated fatty acids with 12-hydroxystearic acid. In some embodiments, (b) is produced by esterifying a mixture of saturated and unsaturated fatty acids with 12-hydroxystearic acid until an acid value of between about 145 mg KOH/g and about 165 mg KOH/g is reached. In some embodiments, the acid value of about 155 mg KOH/g is reached.

In some embodiments, (c) is 12-hydroxystrearic acid.

In some embodiments, (a), (b), or both (a) and (b) are produced from a mixture of saturated and unsaturated fatty acids comprising: (i) 10-20% w/w palmitic acid (C16); (ii) 0.2-5% w/w palmitoleic acid (C16:1); (iii) 10-20% w/w stearic acid (C18); (iv) 40-60% w/w oleic acid (C18:1); (v) 10-20% w/w linoleic acid (C18:2); and (vi) 0.3-5% w/w linolenic acid (C18:3). In some embodiments, the mixture of saturated and unsaturated fatty acids is from: almond oil, olive oil, coconut oil, cocoa tree oil, soybean oil, palm oil, sunflower oil, or any combination thereof (i.e. any combination of at least 2 of these oils, or of at least 3, at least 4, at least 5, at least 6 or all 7 of these oils) (e.g., a combination of olive oil, coconut oil, cocoa tree oil, soybean oil and sunflower oil). In some embodiments, (a), (b) and/or (c) are obtained from vegetable sources. In some embodiments, (a), (b) and/or (c) are obtained from plant sources. In some embodiments, (a), (b) and/or (c) are obtained from vegetable sources.

In some embodiments, the emulsifier has a melting point suitable for cold-process emulsions. In some embodiments, the melting point is below about 48, 47, 46, 45, 44, 43, 42, 41, 40, 39, 38, 37, 36, 35, 34, 33, 32, 31, 30, 29, 28, 27, 26, 25, 24, 23, 22, or 21° C. In some embodiments, the melting point is between about 19° C. and about 48° C.

In some embodiments, about 35-52% w/w of (a), about 40-65% w/w of (b), and about 0.5-6% w/w of (c) are mixed. In some embodiments, the emulsifier is produced by melting (a) at about 70 to about 110° C.; mixing with (c); mixing with (b) until dissolution is obtained; and cooling to a temperature between about 50 to about 70° C. In some embodiments, relative amounts of (a), (b), and (c) are adjusted to produce emulsifiers having viscosity levels between about 2000 cP to about 150,000 cP, more specifically about 3000 cP to about 110,000 cP at 25° C. In some embodiments, (a), (b), and (c) are mixed to produce an emulsifier that is homogenous at room temperature.

In some embodiments, the emulsifier enables stabilization of a W/O emulsion comprising up to 90% w/w water for at least 1 month at 50° C.

In some aspects, the present invention relates to a method for producing a W/O emulsion, the method comprising mixing the emulsifier as defined above, or produced by the above mentioned method, with an oil phase and an aqueous phase. In some embodiments, the method is carried out without a heating step. In some embodiments, the method is carried out at a temperature below about 40° C., below about 35° C., below about 30° C., or below about 25° C. In some embodiments, the method is carried out at a temperature between about 10° C. to about 40° C., between about 15° C. to about 35° C., between about 15° C. to about 30° C., between about 15° C. to about 25° C., or between about 20° C. to about 25° C. In some embodiments, the method further comprises adding a thermolabile active ingredient to the emulsion.

In some aspects, the present invention relates to a kit for producing a water-in-oil emulsion, the kit comprising the emulsifier as defined above, or produced by the above mentioned method, and a suitable container.

Other objects, advantages and features of the present invention will become more apparent upon reading of the following non-restrictive description of specific embodiments thereof, given by way of example only with reference to the accompanying drawings.

General Definitions

Headings, and other identifiers, e.g., (a), (b), (i), (ii), etc., are presented merely for ease of reading the specification and claims. The use of headings or other identifiers in the specification or claims does not necessarily require the steps or elements be performed in alphabetical or numerical order or the order in which they are presented.

In the present description, a number of terms are extensively utilized. In order to provide a clear and consistent understanding of the specification and claims, including the scope to be given such terms, the following definitions are provided.

The use of the word "a" or "an" when used in conjunction with the term "comprising" in the claims and/or the specification may mean "one" but it is also consistent with the meaning of "one or more", "at least one", and "one or more than one".

Throughout this application, the term "about" is used to indicate that a value includes the standard deviation of error for the device or method being employed to determine the value. In general, the terminology "about" is meant to designate a possible variation of up to 10%. Therefore, a variation of 1, 2, 3, 4, 5, 6, 7, 8, 9 and 10% of a value is included in the term "about". Unless indicated otherwise, use of the term "about" before a range applies to both ends of the range.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

As used herein, the term "consists of" or "consisting of" means including only the elements, steps, or ingredients specifically recited in the particular claimed embodiment or claim.

By "pharmaceutically acceptable," "physiologically tolerable," "dermatologically acceptable" and grammatical variations thereof, as they refer to compositions, carriers, diluents, and reagents or other ingredients of the formulation, can be used interchangeably and represent that the materials are capable of being administered without the production of undesirable physiological effects such as rash, burning, irritation or other deleterious effects to such a degree as to be intolerable to the recipient thereof.

As used herein, the term "cosmetically acceptable" and grammatical variations thereof, as they refer to compositions, carriers, diluents, and reagents or other ingredients of the formulation, represent that the materials used and final composition are not irritating or otherwise harmful to the patient in general and to the skin, in particular, and preferably are pleasant and well tolerated with respect to general appearance, pH, color, smell and texture (feel), that they are not, for example, unacceptably sticky (tacky), oily or drying, and that they do spread easily, absorb into the skin at an acceptable rate of absorption, and are generally moisturizing.

As used herein, the term "subject" is intended to include human and non-human animals. Exemplary human subjects include a human patient having a disorder, e.g., a disorder described herein, or a normal subject. The term "non-human animals" includes all vertebrates, e.g., non-mammals (such as chickens, amphibians, reptiles) and mammals, such as non-human primates, domesticated and/or agriculturally useful animals, e.g., sheep, dog, cat, cow, pig, horse, etc.

As used herein, the term "treat" or "treating" a subject having a disorder refers to subjecting the subject to a regimen, e.g., the administration of a composition of the present invention such that at least one symptom of the disorder is cured, healed, alleviated, relieved, altered, remedied, ameliorated, or improved. Treating includes administering an amount effective to alleviate, relieve, alter, remedy, ameliorate, improve or affect the disorder or the symptoms of the disorder. The treatment may inhibit deterioration or worsening of a symptom of a disorder.

"Cold-process", as used herein, refers to methods performed in the absence of heat and/or a heating step, and generally refer to processes that take place under 40° C. For example, emulsifiers of the present invention which are suitable for cold-processes do not have to be pre-melted before being combined with other ingredients to produce water-in-oil emulsions of the present invention. In some embodiments, cold-process refers to a method performed at room temperature (e.g., between about 20° C. and about 25° C.).

"Homogenous" refers to substances and mixtures which are in a single phase.

"Storage stable" includes a composition that maintains its stability during its shelf life for its intended use as an approved cosmetic and/or pharmaceutical product for sale and home use by its intended users.

DESCRIPTION OF ILLUSTRATIVE EMBODIMENTS

The present invention relates to cold-process-compatible emulsifiers that are able to stabilize water-in-oil emulsions. In general, emulsifiers of the present invention comprise homogenous mixtures of: (a) polyglycerol fatty acid esters consisting of saturated and unsaturated fatty acid esters of polyglycerol; (b) polyhydroxystearic acid copolymers consisting of copolymers of hydroxystearic acid with saturated and unsaturated fatty acids; and (c) hydroxystearic acid.

Polyglycerol Fatty Acid Esters

In accordance with the present invention, polyglycerol fatty acid esters comprising or consisting of saturated and unsaturated fatty acid esters of polyglycerol are useful for producing W/O-stabilizing emulsifiers having advantageous properties. As used herein, the expression "polyglycerol fatty acid esters consisting of saturated and unsaturated fatty acid esters of polyglycerol" or more simply "saturated and unsaturated fatty acid esters of polyglycerol" refer to the products obtainable by the trans-esterification reaction between a suitable polyglycerol and an oil mixture rich in unsaturated fatty acids (e.g., using heat and vigorous mixing with basic catalysis) to obtain substituted (e.g., mono-substituted) or more precisely esterified (e.g., mono-esterified) polyglycerols. In some embodiments, such products are referred to as "component A" in accordance with the present invention.

In some embodiments, the suitable polyglycerol can be polyglycerol-n, where n is an integer corresponding to the number of glycerol monomers. In general, the greater the number of glycerol monomers, the more polar the polyglycerol becomes. Without being bound by theory, too great a number of glycerol monomers may lead to polyglycerol molecules that are too polar to be suitable for the emulsifiers of the present invention. Accordingly, in some embodiments, n can be an integer from 2 to 10. In some embodiments, n can be 2, 3, 4, 6 or 10. In some embodiments, n can be 2 to 4. In some embodiments, n can be 2. It would be understood by the skilled person that the expression "polyglycerol-n" refers to the main species of polyglycerol that is present in a preparation, and that other polyglycerols may also be present to a lesser degree. For example, polyglycerol-6 may also contain a broad range of polyglycerols such as polyglycerol 3, 4, 5, 6, 7 and 8, but polyglycerol-6 is the main species that is present. Accordingly, the expression "polyglycerol-n" as used herein is meant to refer to the main species of polyglycerol that is found in a given preparation, but does not necessarily exclude the presence of other polyglycerols in lesser relative amounts, as long as the other polyglycerols do not interfere with the preparation of emulsifiers of the present invention.

As used herein, an "oil mixture rich in unsaturated fatty acids" refers to an oil mixture having at least 50% w/w of mono- and/or poly-unsaturated fatty acids. The presence of unsaturated fatty acids in the polyglycerol fatty acid esters and the polyhydroxystearic acid copolymers described herein provide multiple advantages and functionality to emulsifiers of the present invention. For example, the lower melting point of unsaturated fatty acids compared to saturated fatty acids reduces the melting point of the emulsifiers of the present invention and help render them suitable for cold-process methods/formulations (i.e., methods that are more environmentally friendly or "green"), as well as render them compatible with the addition of thermolabile active agents. Furthermore, unsaturated fatty acids play important roles in skin tissue by participating structurally and functionally in the maintenance of skin homeostasis. Some unsaturated fatty acids are involved in the synthesis of ceramides and thus play important roles in the stratum corneum barrier function. Some unsaturated fatty acids also act as metabolic substrates in the regulation of cutaneous inflammation process. Accordingly, in some embodiments, the inclusion of unsaturated fatty acids provides additional functionality to emulsifiers of the present invention.

In some embodiments, oil mixtures rich in unsaturated fatty acids of the present invention can include only oils from natural sources (e.g., animal or plant (e.g., vegetable sources)). In some embodiments, oil mixtures of the present invention are obtained from almond oil, olive oil, coconut oil, cocoa tree oil, soybean oil, palm oil, sunflower oil, or any combination thereof (i.e. any combination of at least 2 of these oils, or of at least 3, at least 4, at least 5, at least 6 or all 7 of these oils) (e.g., a combination of olive oil, coconut oil, cocoa tree oil, soybean oil and sunflower oil). In some embodiments, oil mixtures of the present invention can include only C16 and/or C18 fatty acids, such as palmitic acid (C16), palmitoleic acid (C16:1), stearic acid (C18), oleic acid (C18:1), linoleic acid (C18:2), and linolenic acid (C18:3). In some embodiments, oil mixtures of the present invention comprise saturated and unsaturated fatty acids according to Table 1. In preferred embodiments, the oil mixture used in the present invention contains the fatty acids listed in Table 1 within the specified ranges.

TABLE 1

| Fatty acids | Range (% w/w) |
|---|---|
| Palmitic acid (C16) | 10-20 |
| Palmitoleic acid (C16:1) | 0.2-5 |
| Stearic acid (C18) | 10-20 |
| Oleic acid (C18:1) | 40-60 |
| Linoleic acid (C18:2) | 10-20 |
| Linolenic acid (C18:3) | 0.3-5 |

Polyhydroxystearic Acid Copolymers

Polyhydroxystearic acid is a solid wax having a high melting point that is commonly prepared by reacting 85% w/w 12-hydroxystearic acid with 15% w/w stearic acid. However, this polymerization reaction is unpredictable, difficult to control, and results in the production of a heterogeneous mixture of homopolymers having a wide range of monomer repeats (e.g., species having monomer lengths of 2, 3, 4, etc.). These types of polyhydroxystearic acid molecules are referred to herein as "polyhydroxystearic acid homopolymers" or simply "homopolymers", and empirical testing by the present inventors has revealed that they are unsuitable for producing water-in-oil-stabilizing emulsifiers of the present invention.

In contrast, in accordance with the present invention, it was surprisingly discovered that polyhydroxystearic acid copolymers of hydroxystearic acid with saturated and unsaturated fatty acids are useful for producing water-in-oil-stabilizing emulsifiers having advantageous properties. In some embodiments, hydroxystearic acid (e.g., 12-hydroxystearic acid) controlled copolymerization is carried out in the presence of an oil mixture rich in unsaturated fatty acids, as defined above. Without being bound by theory, the oil mixture is believed to act as a polymerization controller, resulting in a more homogeneous mixture of molecules and polyhydroxystearic acid copolymers having a lower melting point, as compared to the polyhydroxystearic acid homopolymers mentioned above. Polyhydroxystearic acid copolymers obtainable by esterifying a mixture of saturated and unsaturated fatty acids with hydroxystearic acid (e.g., 12-hydroxystearic acid) in accordance with the present invention are referred to herein as "polyhydroxystearic acid copolymers" or "copolymers of hydroxystearic acid with saturated and unsaturated fatty acids". In some aspects, the present invention relates to such copolymers of hydroxystearic acid with saturated and unsaturated fatty acids, compositions comprising same, as well as methods for producing same as described herein. In accordance with specific embodiments, the polyhydroxystearic acid copolymers of hydroxystearic acid with saturated and unsaturated fatty acids of the invention comprise one or two hydroxystearic acid monomers for each fatty acid (wherein the fatty acids in the copolymers include saturated and unsaturated fatty acids). In a specific embodiment, there is a ratio of 1:1, 1.5:1 or 2:1 hydroxystearic acid monomer(s): fatty acid moiety/chain (wherein the fatty acids in the copolymers include saturated and unsaturated fatty acids). In a specific embodiment, in the copolymers, there are three hydroxystearic acid monomers for two fatty acid moieties/chains (wherein the fatty acids in the copolymers include saturated and unsaturated fatty acids). In another specific embodiment, in the copolymers, there are two hydroxystearic acid monomers for each fatty acid moiety/chain (wherein the fatty acids in the copolymers include saturated and unsaturated fatty acids). In another specific embodiment, in the copolymers, there is one hydroxystearic acid monomer for each fatty acid moiety/chain (wherein the fatty acids in the copolymers include saturated and unsaturated fatty acids).

In some embodiments, copolymers of hydroxystearic acid with saturated and unsaturated fatty acids can be produced by reacting about 0.5 to 0.8 equivalents (preferably about 0.6 equivalents) of 12-hydroxystearic acid with about 1 equivalent of saturated and unsaturated fatty acids (i.e., an oil mixture rich in unsaturated fatty acids). In some embodiments, copolymers of hydroxystearic acid with saturated and unsaturated fatty acids can be produced by esterifying a mixture of saturated and unsaturated fatty acids (i.e., an oil mixture rich in unsaturated fatty acids) with 12-hydroxystearic acid until an acid value of between about 145 mg KOH/g and about 165 mg KOH/g is reached. In some embodiments, an acid value of about 155 mg KOH/g is reached.

Water-in-Oil Stabilizing Emulsifiers

In some aspects, the present invention relates to the discovery of water-in-oil stabilizing emulsifiers having advantageous properties. In some embodiments, emulsifiers of the present invention can stabilize water-in-oil emulsions by acting as a primary emulsifier (i.e., without the need of a co-emulsifier and/or stabilizer). As used herein, a "primary emulsifier" is a substance that is able to stabilize a water-in-oil emulsion when used alone. In contrast, a "co-emulsifier" is a substance that may help another emulsifier stabilize a particular water-in-oil emulsion, but a co-emulsifier is not able to give a stable water-in-oil emulsion when used alone (i.e., without the presence of a primary emulsifier). A "stabilizer" refers to a substance that is able to improve the stability of an emulsion (e.g., give a better result in stability testing). In some embodiments, the stabilizer can include a rheological modifier or salt, which are substances that are able to change the density/viscosity of a liquid (e.g., oil or water). For example, the "rheological modifier" can help an emulsifier stabilize an emulsion by changing the density/viscosity of a liquid (oil or water). The salt's ability to change the surface tension of water may also stabilize a W/O emulsion.

In some embodiments, emulsifiers of the present invention are suitable for cold-process methods/formulations, as the relatively low melting point and homogenous nature of the emulsifiers can preclude the need for pre-melting the emulsifier prior to combining with other materials during the preparation of an emulsion. In some embodiments, emulsifiers of the present invention have a melting point between about 19° C. and about 48° C. In some embodiments, emulsifiers of the present invention have a melting point less than about 48, 47, 46, 45, 44, 43, 42, 41, 40, 39, 38, 37, 36, 35, 34, 33, 32, 31, 30, 29, 28, 27, 26, 25, 24, 23, 22, or 21° C.

Cold-process suitable emulsifiers are advantageous in that cannot only reduce energy consumption and manufacturing costs, but are also compatible with the addition of thermolabile ingredients. As used herein, the expression "thermolabile ingredient" refers to any compound which is not resistant (e.g., is degraded and/or loses its intended function or advantageous property) after being subjected to heating during the preparation of a composition comprising an emulsifier of the present invention (e.g., a water-in-oil emulsion). In some embodiments, thermolabile ingredients of the present invention refer to compounds that are not resistant upon being subjected to temperatures higher than 40° C., 45° C., 50° C., 55° C., 60° C., or 65° C.

In some aspects, water-in-oil-stabilizing emulsifiers of the present invention can be prepared by combining: (a) polyglycerol fatty acid esters consisting of saturated and unsaturated fatty acid esters of polyglycerol; (b) polyhydroxystearic acid copolymers consisting of copolymers of hydroxystearic acid with saturated and unsaturated fatty acids; and (c) hydroxystearic acid (e.g., 12-hydroxystearic acid, which can be derived from natural sources such as hydrogenated ricinoleic acid). In some embodiments, emulsifiers of the present invention can comprise: (a) about 35-52% w/w of the polyglycerol fatty acid esters consisting of saturated and unsaturated fatty acid esters of polyglycerol; (b) about 40-65% w/w of the polyhydroxystearic acid copolymers consisting of copolymers of hydroxystearic acid with saturated and unsaturated fatty acids; and (c) about 0.5-6% w/w of the hydroxystearic acid (e.g., 12-hydroxystearic acid). In some embodiments, emulsifiers of the present invention can comprise (a) polyglycerol fatty acid esters consisting of saturated and unsaturated fatty acid esters of polyglycerol in a range having a lower limit of 35, 36, 37, 38, 39, 40, 41, or 42% w/w and an upper limit of 43, 44, 45, 46, 47, 48, 49, 50, 51, or 52% (w/w). In some embodiments, emulsifiers of the present invention can comprise (b) polyhydroxystearic acid copolymers consisting of copolymers of hydroxystearic acid with saturated and unsaturated fatty acids in a range having a lower limit of 40, 41, 42, 43, 44, 45, 46, 47, 48, 49, 50, 51, or 52% w/w and an upper limit of 53, 54, 55, 56, 57, 58, 59, 60, 61, 62, 63, 64, or 65% w/w. In some embodiments, emulsifiers of the present invention can comprise (c) hydroxystearic acid (e.g., 12-hydroxystearic acid) in a range of 0.5-5%, 1-5%, 1-6%, 2-5%, 3-5%, 4-5%, 1-4%, 1-3%, 1-2%, or 2-4% w/w.

In some embodiments, different final viscosities of emulsifiers of the present invention can be obtained by modulating the percentage of each of the aforementioned components to produce emulsifiers that are flexible (e.g., suitable for a wide range of cold-process applications). In this way, specific emulsifiers can be developed for the manufacturing of stable low viscosity emulsions (e.g., light lotions) or for more structured emulsions (e.g., dense cream, waxes).

In some embodiments, emulsifiers of the present invention can be prepared by melting about 35-52% w/w of (a) polyglycerol fatty acid esters consisting of saturated and unsaturated fatty acid esters of polyglycerol at about 70-110° C. (preferably at about 80° C.); adding about 0.5-6% w/w of (c) hydroxystearic acid (e.g., 12-hydroxystearic acid) and stirring (e.g., for about 30 minutes); and adding about 40-65% w/w of (b) polyhydroxystearic acid copolymers consisting of copolymers of hydroxystearic acid with saturated and unsaturated fatty acids, and stirring until completely dissolved (e.g., about 1 hour); and cooling to obtain a viscous gel (e.g., soft gel, gel or dense gel).

In some embodiments, emulsifiers of the present invention can have the texture of a soft paste, gel (e.g., soft gel, gel or dense gel), or liquid at room temperature (e.g., 25° C.). Such textures are advantageous in that they may not require pre-melting prior to being added to other ingredients for preparing homogeneous compositions of the present invention (e.g., water-in-oil emulsions). In some embodiments, emulsifiers of the present invention can have a viscosity between about 2000 cP to about 150,000 cP, more specifically between about 3000 cP to about 110,000 cP at 25° C. The viscosity of the emulsifiers of the present invention can be measured using a viscometer (e.g., Brookfield viscometer RVDV-I prime RV with Helipath Model D) and can be expressed as centipoise (cP).

In some embodiments, emulsifiers of the present invention are useful for stabilizing water-in-oil emulsions comprising non-polar oils (e.g., mineral oils) as well as polar oils (e.g., at least 1 month at 50° C.), the latter of which is generally considered as being more difficult to stabilize in water-in-oil emulsions. As used herein, "polar" in the context of oils comprised in emulsions of the present invention refers to polarity—i.e., a measure of interfacial tension of each oil. Typical polar oils are fatty alcohols, esters and triglycerides. In some embodiments, the polar oil can include vegetable oils such as olive oil, jojoba oil, germ oil, almond oil, etc.

In some embodiments, emulsifiers of the present invention can include only ingredients from natural sources (e.g., animal or plant/vegetable sources). For example, glycerol can be obtained from vegetable oil saponification processes; diglycerol (polyglycerol-2), triglycerol (polyglycerol-3), tetraglycerol (polyglycerol-4), etc., can be obtained from glycerol dimerization, trimerization, tetramerizartion, etc.; 12-hydroxystearic acid can be obtained from hydrogenated castor oil after a saponification process. In some embodiments, the present invention can include only ingredients that qualify as "natural" or "natural and organic" as established by the Ecocert™ standards.

Water-in-Oil Emulsions and Uses Thereof

Emulsifiers of the present invention can be used for preparing a variety of compositions such as stable water-in-oil emulsions. As used herein, the term "stable", when used in the context of water-in-oil emulsions, refers to the ability of the emulsion to resist phase separation (i.e., between the aqueous phase and the oil phase). Emulsion stability can be measured by visual inspection to determine the length of time that a given emulsion remains stable. In some embodiments, accelerated conditions such as subjecting the emulsion to an elevated temperature (e.g., 50° C.) can be used. In general, an emulsion (e.g., in a cosmetic composition) is considered sufficiently stable for commercial use if it remains stable for at least 1 month at 50° C. In some embodiments, water-in-oil emulsions comprising emulsifiers of the present invention are able to remain stable for at least 1 week, at least 2 weeks, at least 3 weeks, or at least 1 month at a temperature ranging from −15 to 50° C. In some embodiments, water-in-oil emulsions comprising emulsifiers of the present invention are able to remain stable for at least 1 week, at least 2 weeks, at least 3 weeks, or at least 1 month at 50° C. In some embodiments, water-in-oil emulsions comprising emulsifiers of the present invention are able to remain stable following one or more freeze/thaw cycles, for example at least 1, 2, 3, 4, 5 or 6 freeze/thaw cycles. In some embodiments, the freezing step is at a temperature of about −15° C. In some embodiments, the thawing step is at room temperature. i.e., about 20 to 25° C.

In some aspects, the present invention relates to a method for producing a water-in-oil emulsion, the method comprising mixing the emulsifier of the present invention with an oil phase and an aqueous phase. In some embodiments, the method can be carried out without a heating step (e.g., it can be a cold-process method). In some embodiments, the method can be carried out at a temperature below about 40° C., below about 35° C., below about 30° C., or below about 25° C. In some embodiments, the method can be carried out at a temperature between about 10° C. to about 40° C., between about 15° C. to about 35° C., between about 15° C. to about 30° C., between about 15° C. to about 25° C., or between about 20° C. to about 25° C. In some embodiments, the method can comprise adding a thermolabile active ingredient to said emulsion.

Water-in-oil emulsions (e.g., when used in cosmetic compositions) can have undesirable properties such as leaving a strong oily feeling on the skin for an extended period of time and as having a comedogenic effect. In some embodiments, emulsifiers of the present invention can minimize or avoid this undesirable profile by enabling the stabilization of water-in-oil emulsions comprising a high percentage of water. In some embodiments, the performance of a water-in-oil emulsifier can be characterized or expressed in terms of the maximum amount of water in the emulsion that can be stabilized by the emulsifier. In general, if an emulsifier can stabilize a water-in-oil emulsion having e.g., up to 93% water about, then the emulsifier is considered as also being able to stabilize emulsions having water concentrations lower than 93%. In some embodiments, emulsifiers of the present invention can stabilize water-in-oil emulsions comprising about 0.01-94% w/w water. In some embodiments, emulsifiers of the present invention can stabilize water-in-oil emulsions comprising up to 90%, up to 91%, up to 92%, up to 93%, up to 93.5%, or up to 94% w/w water.

In some embodiments, emulsifiers of the present invention or emulsions stabilized by same can be employed in cosmetic compositions or pharmaceutical compositions. In some embodiments, emulsifiers of the present invention or emulsions stabilized by same can be employed in dermatological compositions. In some embodiments, the compositions can by a liquid, cream, gel or wax.

In some aspects, the present invention relates to a kit for producing a water-in-oil emulsion, the kit comprising an emulsifier of the present invention and a suitable container. The kit may further comprise instructions for preparing an emulsion using the emulsifier.

Formulations and Additives

In some embodiments, compositions of the present invention can be in the form of creams, milks, gel creams, fluid lotions, and vaporizable fluid lotions. When the composition according to the present invention possesses appropriate fluidity characteristics, it can also serve for the impregnation of substrates consisting of synthetic or natural, woven or nonwoven textile fibers, or papers, for constituting articles, for example wipes, intended for care, protection or cleaning of the skin, of the scalp or of the hair, or for example papers for sanitary or household use.

In some embodiments, compositions of the present invention can be used by application on the skin, hair or scalp, whether it is direct application in the case of a cosmetic, dermocosmetic, dermo-pharmaceutical or pharmaceutical composition, or indirect application in the case of a product for the care, protection, or cleaning of the body, being in the form of a textile article, for example a wipe, or of paper, for example a paper for sanitary use, intended to be in contact with the skin, hair or scalp.

The present invention also relates to the cosmetic use of the composition as defined herein for cleaning, for protection and/or for care of the skin, hair or scalp. Compositions of the present invention can be used for care or for protection of the skin, for example as cream, as milk or as lotion for care or for protection of the face, hands and body.

In some embodiments, compositions according to the present invention can also be used as a product for protecting the skin against the sun's rays, and as a skin make-up product. In a particular embodiment, compositions according to the present invention can include an ultraviolet absorber. Examples of the ultraviolet absorbers include benzoic acid ultraviolet absorbers such as p-aminobenzoic acid (hereinafter, abbreviated as "PABA"), PABA monoglycerin ester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA ethyl ester; anthranilic acid ultraviolet absorbers such as homomethyl-N-acetyl anthranilate; salicylic acid ultraviolet absorbers such as amyl salicylate, menthyl salicylate, homomethyl salicylate, octyl salicylate, phenyl salicylate, benzyl salicylate, and p-isopropanol phenyl salicylate; cinnamic acid ultraviolet absorbers such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxycinnamate, cyclohexyl-p-methoxycinnamate, ethyl-.alpha.-cyano-.beta.-phenyl cinnamate, 2-ethylhexyl-.alpha.-cyano-.beta.-phenyl cinnamate, and glycerylmono-2-ethylhexanoyl-diparamethoxycinnamate; benzophenone ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethyl hexyl-4'-phenylbenzophenone-2-carboxylate, 2-hydroxy-4-n-octoxybenzophenone, and 4-hydroxy-3-carboxybenzophenone; 3-(4'-methylbenzylidene)-d,l-camphor; 3-benzylidene-d,l-camphor; urocanic acid; ethyl urocanate ester; 2-phenyl-5-methylbenzoxazole; 2,2'-hydroxy-5-methylphenylbenzotriazole; 2-(2'-hydroxy-5'-t-octylphenyl)benzotriazole; 2-(2'-hydroxy-5'-methylphenyl)benzotriazole; dibenzalazine; dianisoylmethane; 4-methoxy-4'-t-butyldibenzoylmethane; 5-(3,3-dimethyl-2-norbornylidene)-3-pentan-2-one; 2,4,6-trianilino-p-(carbo-2'-ethylhexyl-1'-oxy)-1,3,5-triazine; and 4-tert-butyl-4'-methoxydibenzoylmethane. These ultraviolet absorbers may be used alone or in a combination of two or more thereof.

In some embodiments, compositions of the present invention can include a moisturizer. Examples of moisturizers include polyethylene glycol (PEG1500), propylene glycol, 1,3-propanediol, 3-methyl-1,3-butanediol, glycerol, 1,3-butylene glycol, xylitol, sorbitol, maltitol, chondroitin sulfuric acid, hyaluronic acid, mucoitin sulfuric acid, Trichosanthis semen acid, atelocollagen, cholesteryl-12-hydroxy stearate, sodium lactate, urea, bile salt, dl-pyrrolidone carboxylate, short-chain soluble collagen, diglycerin (EO) PO adducts, *Rosa roxburghii* extracts, yarrow extracts and melilot extracts. These moisturizers may be used alone or in a combination of two or more thereof.

In some embodiments, compositions of the present invention can include a thickener. Examples of thickeners include microcrystalline wax, zinc stearate, gum arabic, carrageenan, Karaya gum, gum tragacanth, carob gum, quince seed (marmelo), casein, dextrin, gelatin, sodium pectinate, sodium alginate, methylcellulose, ethylcellulose, CMC, hydroxyethyl cellulose, hydroxypropyl cellulose, PVA, PVM, PVP, sodium polyacrylate, carboxyvinyl polymer, locust bean gum, guar gum, tamarind gum, dialkyl dimethyl ammonium cellulose sulfate, xanthan gum, magnesium aluminum silicate, bentonite, hectorite, quaternary ammonium salt-based cation-modified bentonite, quaternary ammonium salt-based cation-modified hectorite, and decaglycerin fatty acid ester eicosadioate condensate. These thickeners may be used alone or in a combination of two or more thereof. In some embodiments, compositions of the present invention can comprise a thickener which is microcrystalline wax and/or zinc stearate.

In some embodiments, compositions of the present invention can include a preservative. Without being so limited, preservative are ingredients capable of retarding or preventing microbial or chemical spoilage and protecting against discoloration, such as DMDM hydantoin, methylparaben, propylparaben, phenoxyethanol, ethylparaben, butylparaben, imidazolidinyl urea, diazolidinyl urea, quaternium-8, quaternium-14, quaternium-15, propylene glycol, dehydroacetic acid, methylchloroisothiazolinone, methylisothiazolinone and germaben. These preservatives may be used alone or in a combination of two or more thereof.

In some embodiments, compositions of the present invention can include a pH adjuster. Examples of pH adjusters include edetic acid, disodium edetate, citric acid, sodium citrate, sodium hydroxide, potassium hydroxide, and triethanolamine. These pH adjusters may be used alone or in a combination of two or more thereof.

In some embodiments, compositions of the present invention can include a plant or algae extract. Examples of plant extracts include extracts of: aloe vera, artichoke, bamboo, bearberry, birch tree, borage, butcher's broom, capsicum, centella, chamomile, coffee, cucumber, devil's claw, dragonfruit, eucalyptus, fenugreek, flax, ginger, ginseng, grapefruit, green tea, *Hamamelis*, hawthorn, honeysuckle, hops, horse chestnut tree, horsetail, iris, jasmine, jojoba, kidney bean, kola, lavender, lemon, liquorice, lotus, magnolia tree, marshmallow, milk thistle, millet, myrrh tree, neem tree, noni tree, oat, olive tree, orchid, oregano, passion fruit, peppermint, pineapple, pomegranate tree, quinoa, raspberry bush, red clover, rice, rose, rose hips, rosemary, sage, saw palmetto, schizandra, sea fennel, sesame, strawberry, sunflower, thyme, tomato, turmeric, violet, walnut tree, watercress, wheat, white water lily, white willow, winter cherry, witch hazel, ylang-ylang, and yucca extracts. Examples of algae extracts include: bladderwrack, devil's apron, dulse, dunaliella, himanthalia, laminaria, pelvetia, porphyra, and spirulina extracts.

In some embodiments, compositions of the present invention can include an antioxidant. Examples of antioxidants include, but are not limited to, amino acids such as glycine, histidine, tyrosine, trytophan and derivatives thereof, imidazoles such as urocanic acid and derivatives thereof, peptides, such as D,L-carnosine, D-carnosine, L-carnosine and derivatives thereof such as anserine, carotinoids, carotenes such as .alpha.-carotone, .beta.-carotene, lycopene, and derivatives thereof, chlorogenic acid and derivatives thereof, lipoic acid and derivatives thereof such as dihydrlipoic acid, aurothioglycose, propylthiouracil and other thiols such as thioredoxin, glutathione, cysteine, cystine, cystamine and glycosyl, N-acetyl, methyl, ethyl, propyl, amyl, butyl, lauryl, palmitoyl, oleyl, .alpha.-linoleyl, cholesteryl and glyceryl esters and salts thereof, dilauryl thiodipropionate, distearyl thiodipropionate, thiodipropionic acid and derivatives thereof such as esters, ethers, peptides, lipids, nucleotides, nucleosides, and salts, sulfoximine compounds such as buthionine sulfoximines, homocysteine sulfoximine, buthionine sulfones, penta-, hexa-, hepta-thionine sulfoximine, unsaturated fatty acids and derivatives thereof such as .alpha.-linolenic acid, linoleic acid, oleic acid, folic acid and derivatives thereof, ubiquinone and ubiquinol and derivatives thereof, vitamin C and derivatives thereof such as ascorbyl palmitate, magnesium ascorbyl phosphate, ascorbyl acetate, tocopherals and derivatives such as vitamin E acetate, vitamin A and derivatives such as vitamin A palmitate, vitamin B and derivatives thereof, coniferyl benzoate of benzoin resin, rutinic acid and derivatives thereof, .alpha.-glycosylrutin, ferulic acid, furfurylidene glucitol, carnosine, butyl hydroxytoluene, trihydroxy-butyrophenone, uric acid and derivatives thereof, mannose and derivatives thereof, superoxide dismutase, zinc and derivatives thereof such as ZnO, $ZnSO_4$, selenium and derivatives thereof such as selenium methionine, stilbene and derivatives thereof such as stilbene oxide, trans-stilbene oxide and the like. In particular exemplary embodiments, the one or more antioxidants may include vitamin B, nordihydroguaiaretic acid, butylated hydroxyanisole (BHA), butylated hydroxytoluene (BHT), propyl gallate, erythorbate acid, sodium erythorbate, ascorbir palmitate, ascorbir stearate, butyl hydroxyanisole, and gallic esters. These antioxidants may be used alone or in a combination of two or more thereof.

In some embodiments, compositions of the present invention can include chelating agents or sequestering agents (sequestrants). Examples of chelating agents include EDTA, disodium EDTA, trisodium EDTA, EGTA, disodium EGTA, trisodium EGTA, citric acid, phosphoric acid, and succinic acid.

In some embodiments, compositions of the present invention can include opacifying agents. Examples of pacifying agents include higher fatty alcohols such as cetyl, stearyl, cetostearyl alcohol, arachidyl and behenyl alcohols, solid esters such as cetyl palmitate, glyceryl laurate, stearamide MEA-stearate, high molecular weight fatty amides and alkanolamides and various fatty acid derivatives such as propylene glycol and polyethylene glycol esters. In other embodiments, opacifying agents may include inorganic materials such as, for example, magnesium aluminum silicate, zinc oxide, titanium dioxide or other sunblocking agents.

In some embodiments, compositions of the present invention can include one or more further topically active ingredients useful in skincare. Such active ingredients may include one or more of the following: antimicrobial or antibacterial compounds, for example selected from the following: triclosan, neomycin, clindamycin, polymyxin, bacitracin, benzoyl peroxide, hydrogen peroxide, tetracylines such as doxycycline or minocycline, sulfa drugs such as sulfacetamide, penicillins, cephalosporins such as cephaiexin, and quinolones such as lomefloxacin, olfoxacin or trovafloxacin; antiviral compounds, for example selected from acyclovir, tamvir, and penciclovir; antifungal compounds, for example selected from the following: framesol, clotrimazole, ketoconazole, econazole, fluconazole, calcium or zinc undecylenate, undecylenic acid, butenafine hydrochloride, ciclopirox olaimine, miconazole nitrate, nystatin, sulconazole, and terbinafine hydrochloride; anti-inflammatory compounds, for example selected from the following: steroidal agents selected from hydrocortisone, fluocinolone acetonide, halcinonide, halobetasol propionate, clobetasol propionate, betamethasone dipropionate, betamethasone valerate, and triamcinolone acetonide, and non-steroidal anti-inflammatory agents selected from aspirin, ibuprofen, ketoprofen, naproxen, aloe vera gel, aloe vera, licorice extract, pilewort or zinc; anthelmintic compounds, for example metronidazole.

In some embodiments, compositions of the present invention can include a fragrance. Examples of fragrance include plant perfumes such as rose oil, jasmine oil, and lavender oil; and synthetic perfumes such as limonene, citral, linalool, and eugenol. These perfumes may be used alone or in a combination of two or more thereof.

Active and functional ingredients for use in compositions of the present invention, including those listed above, may be plant extracts, algae extracts, fruit extracts, vegetable extracts, leguminous plant extracts, ferments, proteolytic hydrolysates, peptides, yeast extracts and its derivatives, microorganism extracts, animal derivative extracts and/or synthetic compounds.

The present invention is illustrated in further details by the following non-limiting examples.

EXAMPLES

Example 1

Preparation of Raw Materials and Individual Components

Ingredients and raw materials of the emulsifiers and emulsions of the present invention can be prepared in accordance with the following examples.

Example 1.1: Oil Mixture Rich in Unsaturated Fatty Acids

Olive oil, coconut oil, cocoa tree oil, soybean oil and sunflower oil were mixed to obtain a weight by weight % of saturated and unsaturated fatty acids according to Table 2.

TABLE 2

| Fatty acids | Range (% w/w) |
| --- | --- |
| Palmitic acid (C16) | 10-20 |
| Palmitoleic acid (C16:1) | 0.2-5 |
| Stearic acid (C18) | 10-20 |
| Oleic acid (C18:1) | 40-60 |
| Linoleic acid (C18:2) | 10-20 |
| Linolenic acid (C18:3) | 0.3-5 |

The above oils were obtained from Oleon and other standard suppliers.

Example 1.2: Component A—Polyglycerol Fatty Acid Esters Consisting of Saturated and Unsaturated Fatty Acid Esters of Polyglycerol Polyglycerol fatty acid esters consisting of saturated and unsaturated fatty acid esters of polyglycerol were prepared by mixing the ingredients described below in the presence of a suitable trans-esterification catalyst (KOH) under vigorous stirring and heating the mixture up to 130° C. for 3 hours:

Component A1—Saturated and unsaturated fatty acid esters with polyglycerol-2: 45 g mixture of oils rich in unsaturated fatty acids (see Example 1.1) was trans-esterified (i.e., mono-esterified) with 21 g of polyglycerol-2 (P2) to obtain mono-substituted polyglycerol-2.

Component A2—Saturated and unsaturated fatty acid esters with polyglycerol-3: 45 g mixture of oils rich in unsaturated fatty acids (see Example 1.1) was trans-esterified (i.e., mono-esterified) with 28 g of polyglycerol-3 (P3) to obtain mono-substituted polyglycerol-3.

Component A3—Saturated and unsaturated fatty acid esters with polyglycerol-4: 45 g mixture of oils rich in unsaturated fatty acids (see Example 1.1) was trans-esterified (i.e., mono-esterified) with 35 g of polyglycerol-4 (P4) to obtain mono-substituted polyglycerol-4.

Component A4—Saturated and unsaturated fatty acid esters with polyglycerol-6: 45 g mixture of oils rich in unsaturated fatty acids (see Example 1.1) was transesterified (i.e., mono-esterified) with 39 g of polyglycerol-6 (P6) to obtain mono-substituted polyglycerol-6.

Component A5—Saturated and unsaturated fatty acid esters with polyglycerol-10: 45 g mixture of oils rich in unsaturated fatty acids (see Example 1.1) was transesterified (i.e., mono-esterified) with 45 g of polyglycerol-10 (P10) to obtain mono-substituted polyglycerol-10.

Polyglycerols were obtained from Solvay and Lonza.

In this example, to obtain an oil mixture rich in unsaturated fatty acids having the fatty acid percentages as indicated in Table 2, an oil mixture was used comprising: 60% olive oil, 10% soybean oil, 10% sunflower oil, 10% cocoa tree oil, and 10% coconut oil. However, other oil mixtures can also be used to obtain fatty acid percentages as indicated in Table 2.

Example 1.3: Component B—Polyhydroxystearic Acid Copolymers Consisting of Copolymers of Hydroxystearic Acid with Saturated and Unsaturated Fatty Acids Polyhydroxystearic acid copolymers consisting of copolymers of hydroxystearic acid with saturated and unsaturated fatty acids (component B) were prepared by esterifying 56 g (1 equivalent) of an oil mixture rich in unsaturated fatty acids prepared as described in Example 1.2 with 32 g (0.6 equivalent) of 12-hydroxystearic acid until a final acid value between about 145 mg KOH/g and about 165 mg KOH/g, preferably about 155 mg KOH/g, was obtained. The resulting polyhydroxystearic acid copolymers consisting of copolymers of hydroxystearic acid with saturated and unsaturated fatty acids comprise mono-esterified hydroxystearic acid.

Example 1.4: Component C—12-Hydroxystearic Acid 12-hydroxystearic acid (component C) was obtained from Sigma-Aldrich.

Example 2

Preparation of Emulsifiers having Gel-Like Texture

Emulsifiers having gel-like textures were prepared by reacting components A, B and C as described below:

Emulsifier P2: 45 g of component A1 was melted at about 70° C. to about 110° C., preferably at about 80° C., and 1 g of component C was added under vigorous stirring for about 30 minutes. 45 g of component B was then added followed by stirring until completely dissolved (about 1 hour). The mixture was cooled quickly to obtain a viscous gel that was able to keep its consistency over time (i.e., for more than 4 years) without any phase separation (w/w amounts of the components A, B and C were therefore about as follows: 49.4%; 49.4%; 1.2%). Melting range: 20-21° C.; Appearance: soft gel liquid at room temperature.

Emulsifier P3: 42 g of component A2 was melted at about 70° C. to about 110° C., preferably at 80° C., and 1 g of component C was added under vigorous stirring for about 30 minutes. 45 g of component B was then added followed by stirring until completely dissolved (about 1 hour). The mixture was cooled quickly to obtain a viscous gel that was able to keep its consistency over time, without any phase separation (w/w amounts of the components A; B and C were therefore about as follows: 47.7%; 51.1%; 1.2%). Melting range: 25-26° C.; Appearance: soft gel.

Emulsifier P4: 40 g of component A3 was melted at about 70° C. to about 110° C., preferably at about 80° C., and 1 g of component C was added under vigorous stirring for about 30 minutes. 45 g of component B was then added followed by stirring until completely dissolved (about 1 hour). The mixture was cooled quickly to obtain a viscous gel that was able to keep its consistency over time, without any phase separation (w/w amounts of the components A, B and C were therefore about as follows: 46.5%; 52.3%; 1.2%). Melting range: 30-33° C.; Appearance: soft gel.

Emulsifier P6: 38 g of component A4 was melted at about 70° C. to about 110° C., preferably at about 80° C., and 1 g of component C was added under vigorous stirring for about 30 minutes. 45 g of component B was then added followed by stirring until completely dissolved (about 1 hour). The mixture was cooled quickly to obtain viscous gel that was able to keep its consistency over time, without any phase separation (w/w amounts of the components A, B and C were therefore about as follows: 45.2%; 53.6%; 1.2%). Melting range: 35-37° C.; Appearance: gel.

Emulsifier P10: 30 g of component A5 was melted at about 70° C. to about 110° C., preferably at about 80° C., and 1 g of component C was added under vigorous stirring for about 30 minutes. 45 g of component B was then added followed by stirring until completely dissolved (about 1 hour). The mixture was cooled down quickly to obtain viscous gel that was able to keep its consistency over time, without any phase separation (w/w amounts of the components A; B and C were therefore about as follows: 39.5%; 59.2%; 1.3%). Melting range: 40-44° C.; Appearance: dense gel.

Example 3

Preparation of Emulsifiers Having Different Viscosities

Homogeneous water-in-oil stabilizing emulsifiers having different viscosities were prepared according to Table 3, by varying the relative amounts of components A, B and C. Viscosity of the different emulsifiers was measured with a Brookfield viscometer RVDV-I prime RV with Helipath™ Model D.

TABLE 3

| Component A1 + Component B + Component C (% w/w) | Viscosity at 25° C. |
|---|---|
| 50% + 49% + 1% | 3,000 cP |
| 48% + 50% + 2% | 22,000 cP |
| 45% + 50% + 5% | 110,000 cP |

Example 4

Test of Example 2 Emulsifiers Versus Individual Components

Emulsifiers prepared as described in Example 2 were tested versus individual components for their ability to stabilize a water-in-oil emulsion. The emulsion used for the stability testing was prepared according to Table 4.

TABLE 4

| Water Phase (Phase A): | |
|---|---|
| Aqua | Up to 100% w/w |
| Glycerin | 5% w/w |
| MgSO$_4$ | 1% w/w |
| Phenoxyethanol and Parabens | 0.5% w/w |
| Oil Phase (Phase B): | |
| Jojoba Oil | 2% w/w |
| Isononyl Isononanoate | 10% w/w |
| Paraffinum liquidum | 5.5% w/w |
| Coco-caprylate/caprate | 6% w/w |
| Microcrystalline Wax | 2% w/w |
| Zinc Stearate | 1% w/w |
| Emulsifier/compound* | 3% w/w |

*The following emulsifiers/compounds were tested for their ability to stabilize the emulsion according to Table 4: Emulsifier P2, emulsifier P3, emulsifier P4, emulsifier P6, and emulsifier P10 (each prepared as described in Example 2), components A1-A5 each prepared as described in Example 1.2), component B (prepared as described in Example 1.3), component C 12-hydroxystearic acid (obtained as described in Example 1.4) and polyhydroxystearic acid (prepared by homopolymerization of 12-hydroxystearic acid). Glycerin was used as a humectant; MgSO$_4$ was used as a stabilizer; phenoxyethanol and parabens were added as preservatives; Jojoba oil, isononyl isononanoate, paraffinum liquidum, and coco-caprylate/caprate were used as oil phase emollients; and microcrystalline wax and zinc stearate were used as rheological modifiers/thickeners.

The water (Phase A) and oil (Phase B) phases were heated at about 75° C., and then Phase B was added to Phase A and homogenized for 5 minutes. The mixture was cooled under gentle stirring and emulsion stability was evaluated by visual inspection upon incubation of the various emulsions at 50° C. The results are shown in Table 5.

Example 5

Test of Example 2 Emulsifiers Versus Other W/O Emulsifiers

Emulsifiers prepared as described in Example 2 were tested versus other emulsifiers for their ability to stabilize a water-in-oil emulsion. The emulsion used for the stability testing was prepared according to Table 5.1.

TABLE 5.1

| Water Phase (Phase A): | |
|---|---|
| Aqua | Up to 100% w/w |
| Glycerin | 5% w/w |
| MgSO$_4$ | 1% w/w |
| EDTA | 0.05% w/w |
| Phenoxyethanol and Parabens | 0.5% w/w |
| Oil Phase (Phase B): | |
| *Simmondsia Chinensis* (Jojoba) Oil | 2% w/w |
| Isononyl Isononanoate | 8% w/w |
| Paraffinum liquidum | 8% w/w |
| Coco-caprylate/caprate | 6% w/w |
| Zinc Stearate | 1% w/w |
| Emulsifier/compound* | 5% w/w |

*The following emulsifiers/compounds were tested for their ability to stabilize the emulsion according to Table 5.1: Emulsifier P2, emulsifier P3, emulsifier P4, emulsifier P6, and emulsifier P10 (each prepared as described in Example 2), polyglyceryl-2 polyhydroxystearate, polyglyceryl-2 oleate, diisostearoyl polyglyceryl-3 dimer dilinoleate, polyglyceryl-3 oleate, polyglyceryl-2 isostearate, and sorbitan oleate. Glycerin was used as a humectant; MgSO$_4$ was used as a stabilizer; EDTA was used as a chelating agent; phenoxyethanol and parabens were added as preservatives; Jojoba oil, isononyl isononanoate, paraffinum liquidum, and coco-caprylate/caprate were used as oil phase emollients; zinc stearate was used as rheological modifier/thickener.

The water (Phase A) and oil (Phase B) phases were heated at about 75° C., and then Phase B was added to Phase A and homogenized for 5 minutes. The mixture was cooled under gentle stirring and emulsion stability was evaluated by visual inspection upon incubation of the various emulsions at 50° C. The results are shown in Table 6.

TABLE 5

| Emulsion | 1 week | 2 weeks | 3 weeks | 1 month | 2 months | 3 months |
|---|---|---|---|---|---|---|
| Example 2 Emulsifier P2 | Ok | Ok | Ok | Ok | Ok | Ok |
| Example 2 Emulsifier P3 | Ok | Ok | Ok | Ok | Ok | Ok |
| Example 2 Emulsifier P4 | Ok | Ok | Ok | Ok | Ok | Ok |
| Example 2 Emulsifier P6 | Ok | Ok | Ok | Ok | Ok | Ok |
| Example 2 Emulsifier P10 | Ok | Ok | Ok | Ok | Ok | Ok |
| Example 1.2 component A1 | Ok | Ok | Ok | / | / | / |
| Example 1.2 component A2 | Ok | Ok | Ok | / | / | / |
| Example 1.2 component A3 | Ok | Ok | / | / | / | / |
| Example 1.2 component A4 | Ok | / | / | / | / | / |
| Example 1.2 component A5 | Ok | / | / | / | / | / |
| Polyhydroxystearic acid | Emulsion break after 1 day | | | | | |
| 12-hydroxystearic acid (component C) | Emulsion break after 1 day | | | | | |
| Example 1.3 component B | Emulsion break after 1 day | | | | | |

/ = break

TABLE 6

| Emulsion | 1 week | 2 weeks | 3 weeks | 1 Month |
|---|---|---|---|---|
| Example 2 Emulsifier P2 | Ok | Ok | Ok | Ok |
| Example 2 Emulsifier P3 | Ok | Ok | Ok | Ok |
| Example 2 Emulsifier P4 | Ok | Ok | Ok | Ok |
| Example 2 Emulsifier P6 | Ok | Ok | Ok | Ok |
| Example 2 Emulsifier P10 | Ok | Ok | Ok | Ok |
| Polyglyceryl-2 polyhydroxystearate | Ok | Ok | / | / |
| Polyglycerol-2 oleate | Ok | Ok | / | / |
| Diisostearoyl Polyglyceryl-3 dimer dilinoleate | Ok | Ok | Ok | / |
| Polyglyceryl-3 oleate | Emulsion break after 1 day | | | |
| Polyglyceryl-2 isostearate | Emulsion break after 1 day | | | |
| Sorbitan oleate | Emulsion break after 1 day | | | |

/ = emulsion break

The following components used in Table 6 were prepared as described below:

Polyglyceryl-2 polyhydroxystearate: Under vacuum, hydroxystearic acid was heated to 100° C. in the presence of 0.1% p/p of $H_2SO_4$, allowed to react for 2 hours until the acid value went from about 200 mg KOH/g to 100 mg KOH/g obtain a dimer. 1 mol of hydroxystearic acid dimer was added to 1 mol of polyglycerol-2 under stirring. 0.1% p/p of $H_2SO_4$ (98% p/p) was added and the mixture was heated under vacuum to 140° C. for 3 hours. The final acid value was <3 mg KOH/g.

Polyglycerol-2 oleate: 1 equivalent of polyglycerol-2 was added under vigorous stirring to 1 equivalent of oleic acid, 0.1% p/p of $H_2SO_4$ (98% p/p) was added and the mixture was heated to 160° C. for two hours under vacuum. The final acid value was <3 mg KOH/g.

Diisostearoyl Polyglyceryl-3 dimer dilinoleate: Under vacuum, linoleic acid was heated to 100° C. in the presence of 0.2 equivalent of $HClO_4$ 20% p/p and allowed to react for 8 hours until the acid value went from about 200 mg KOH/g to 100 mg KOH/g to obtain a dimer. To 1 mol of polyglycerol-3, 2 mol of linoleic acid dimer and 2 mol of isostearic acid were added under stirring. 0.1% p/p of $H_2SO_4$ (98% p/p) was added and heated under vacuum to 170° C. for 3 hours. The final acid value: <3 mg KOH/g.

Polyglyceryl-3 oleate: 1 equivalent of polyglycerol-3 was added under vigorous stirring to 1 equivalent of oleic acid, 0.1% p/p of $H_2SO_4$ (98% p/p) was added and the mixture was heated to 160° C. for two hours under vacuum. The final acid value was <3 mg KOH/g.

Polyglyceryl-2 isostearate: At 80° C., 1 equivalent of polyglycerol-2 was added under vigorous stirring to 1 equivalent of isostearic acid, 0.1% p/p of $H_2SO_4$ (98% p/p) was added and the mixture was heated to 160° C. for two hours under vacuum. The final acid value was <3 mg KOH/g.

Sorbitan oleate: 0.1% p/p of $H_2SO_4$ (98% p/p) was added to sorbitol 98% (Sigma-Aldrich), and the mixture was heated at 150° C. under vacuum for 2 hours to obtain Sorbitan. The mixture was cooled, and 1 equivalent of oleic acid and 0.4% p/p of NaOH were added, followed by heating again to 150° C. and the mixture was allowed to react for 2 hours under vacuum. The final acid value was <3 mg KOH/g.

Example 6

Test of Example 2 Emulsifiers in the Presence of a Polar Oil (Sweet Almond Oil) vs. Other W/O Emulsifiers Emulsifiers prepared as described in Example 2 were tested versus other emulsifiers for their ability to stabilize a water-in-oil emulsion in the presence of a polar oil (sweet almond oil). The emulsion used for the stability testing was prepared according to Table 7.

TABLE 7

| Water Phase (Phase A): | |
|---|---|
| Aqua | Up to 100% w/w |
| Glycerin | 5% w/w |
| $MgSO_4$ | 1% w/w |
| Phenoxyethanol and Parabens | 0.5% w/w |
| Oil Phase (Phase B): | |
| Sweet almond oil | 10% w/w |
| Paraffinum liquidum | 15% w/w |
| Emulsifier/compound* | 5% w/w |

*The following emulsifiers/compounds were tested for their ability to stabilize the emulsion according to Table 7: Emulsifier P2, emulsifier P3, emulsifier P4, emulsifier P6, and emulsifier P10 (each prepared as described in Example 2), polyglyceryl-3 oleate, polyglyceryl-2 isostearate and a polyglycerol-based emulsifier (Diisostearoyl Polyglyceryl-3 dimer dilinoleate). Glycerin was used as a humectant; $MgSO_4$ was used as a stabilizer; phenoxyethanol and parabens were added as preservatives; sweet almond oil and paraffinum liquidum were used as oil phase emollients.

The water (Phase A) and oil (Phase B) phases were heated at about 75° C., and then Phase B was added to Phase A and homogenized for 5 minutes. The mixture was cooled under gentle stirring and emulsion stability was evaluated by visual inspection upon incubation of the various emulsions at 50° C. The results are shown in Table 8.

TABLE 8

| Emulsion | 1 week | 2 weeks | 3 weeks | 1 Month |
|---|---|---|---|---|
| Example 2 Emulsifier P2 | Ok | Ok | Ok | Ok |
| Example 2 Emulsifier P3 | Ok | Ok | Ok | Ok |
| Example 2 Emulsifier P4 | Ok | Ok | Ok | Ok |
| Example 2 Emulsifier P6 | Ok | Ok | Ok | Ok |
| Example 2 Emulsifier P10 | Ok | Ok | Ok | Ok |
| Polyglyceryl-3 oleate | Emulsion break after 1 day | | | |
| Polyglyceryl-2 isostearate | Emulsion break after 1 day | | | |
| Diisostearoyl Polyglyceryl-3 dimer dilinoleate | Ok | Emulsion break | / | / |

Example 7

Test of Example 2 Emulsifiers in a Cold-Process Method Emulsion

Emulsifiers prepared as described in Example 2 were tested for their ability to stabilize a water-in-oil emulsion under cold-process conditions and compared to other emulsifiers. The emulsion used for the stability testing was prepared according to Tables 9A and 9B.

TABLE 9A

| Water Phase (Phase A): | |
|---|---|
| Aqua | Up to 100% w/w |
| Glycerin | 5% w/w |
| MgSO$_4$ | 1% w/w |
| Phenoxyethanol and Parabens | 0.5% w/w |
| Oil Phase (Phase B): | |
| Paraffinum liquidum | 25% w/w |
| Emulsifier* | 5% w/w |

TABLE 9B

| Water Phase (Phase A) | |
|---|---|
| Aqua | Up to 100.00% w/w |
| Glycerin | 5% w/w |
| MgSO$_4$ | 1% w/w |
| Phenoxyethanol and Parabens | 0.5% w/w |
| Oil Phase (Phase B) | |
| Magnesium Stearate | 0.3% w/w |
| *Simmondsia Chinensis* (Jojoba) Seed Oil | 2% w/w |
| Isononyl isonanoate | 8.7% w/w |
| Paraffinum liquidum | 8% w/w |
| Coco-Caprylate/Caprate | 6% w/w |
| Emulsifier/compound* | 5% w/w |

*Tested emulsifiers: Table 9A: Emulsifier P2, emulsifier P3, emulsifier P4, emulsifier P6, and emulsifier P10 (each prepared as described in Example 2); Table 9B: Emulsifier P2, emulsifier P3, emulsifier P4, emulsifier P6, and emulsifier P10 (each prepared as described in Example 2), polyglyceryl-3 oleate, polyglyceryl-2 isostearate, diisostearoyl polyglyceryl-3 dimer dilinoleate and Polyglyceryl-2 polyhydroxystearate. Glycerin was used as a humectant; MgSO$_4$ was used as a stabilizer; phenoxyethanol and parabens were added as preservatives; magnesium stearate was used as rheological modifier/thickener; paraffinum liquidum (Table 9A), or a mixture of paraffinum liquidum, *Simmondsia chinensis* (Jojoba) seed oil, isononyl isonanoate and coco-caprylate/caprate (Table 9B), was used as an oil phase emollient.

Phase A was added to Phase B at room temperature (about 25° C.) homogenizing for 5 minutes. In this example, both phases were prepared without heating: it was a completely cold process. Stability was evaluated by visual inspection upon incubation of the various emulsions at 50° C. and the results are shown in Tables 10A and 10B.

TABLE 10A

Stability of emulsions of Table 9A

| Emulsion | 1 week | 2 weeks | 3 weeks | 1 Month |
|---|---|---|---|---|
| Example 2 Emulsifier P2 | Ok | Ok | Ok | Ok |
| Example 2 Emulsifier P3 | Ok | Ok | Ok | Ok |
| Example 2 Emulsifier P4 | Ok | Ok | Ok | Ok |
| Example 2 Emulsifier P6 | Ok | Ok | Ok | Ok |
| Example 2 Emulsifier P10 | Ok | Ok | Ok | Ok |

TABLE 10B

Stability of emulsions of Table 9B

| Emulsion | 1 week | 2 weeks | 3 weeks | 1 Month |
|---|---|---|---|---|
| Example 2 Emulsifier P2 | Ok | Ok | Ok | Ok |
| Example 2 Emulsifier P3 | Ok | Ok | Ok | Ok |
| Example 2 Emulsifier P4 | Ok | Ok | Ok | Ok |
| Example 2 Emulsifier P6 | Ok | Ok | Ok | Ok |
| Example 2 Emulsifier P10 | Ok | Ok | Ok | Ok |
| Polyglyceryl-3 Oleate | Emulsion breaks at t0 | | | |
| Polyglyceryl-2 Isostearate | Emulsion breaks at t0 | | | |
| Diisostearoyl Polyglyceryl-3 Dimer Dilinoleate | Ok | Ok | Ok | Ok |
| Polyglyceryl-2 Dipolyhydroxystearate | Ok | Ok | Emulsion breaks | / |

Example 8

Test of Example 2 Emulsifiers in a Cold-Process Method Emulsion with Up to About 94% of Water Phase Emulsifiers prepared as described in Example 2 were tested for their ability to stabilize a water-in-oil emulsion comprising a high percentage of water (about 94% w/w). The emulsion used for the stability testing was prepared according to Table 11.

TABLE 11

| Water Phase (Phase A): | |
|---|---|
| Aqua | Up to 100% w/w |
| Thickener** | 0.5% w/w |
| Phenoxyethanol and Ethylhexylglycerin | 0.5% w/w |
| Oil Phase (Phase B): | |
| Almond Oil | 4% w/w |
| Emulsifier* | 1.5% w/w |

*Tested emulsifiers: Emulsifier P2, emulsifier P3, emulsifier P4, emulsifier P6, and emulsifier P10 (each prepared as described in Example 2). In the above emulsion, phenoxyethanol and ethylhexylglycerin were added as preservatives, and the tested thickeners** were: Sodium-Polyacrylate, Sodium-Carbomer and Hydroxyethyl-cellulose. Almond oil was used as emollient.

Phase B was added to Phase A at room temperature (about 25° C.) homogenizing for 1 minute. At the end of the process, the emulsion was gently stirred for about 10 minutes. In this example, both phases were prepared without heating: it was a completely cold process. Stability was tested for each emulsifier with each thickener by visual inspection at 50° C. and the general results (for all the tested thickeners) are shown in Table 12.

TABLE 12

| Emulsion | 1 week | 2 weeks | 3 weeks | 1 Month |
|---|---|---|---|---|
| Example 2 Emulsifier P2 | Ok | Ok | Ok | Ok |
| Example 2 Emulsifier P3 | Ok | Ok | Ok | Ok |
| Example 2 Emulsifier P4 | Ok | Ok | Ok | Ok |
| Example 2 Emulsifier P6 | Ok | Ok | Ok | Ok |
| Example 2 Emulsifier P10 | Ok | Ok | Ok | Ok |

Example 9

Silicon Oil Compatibility of the Example 2 Emulsifiers

Emulsifiers prepared as described in Example 2 were tested for their ability to stabilize water-in-oil emulsions in the presence of a high amount of silicon oil (cyclopentasiloxane, cyclohexasiloxane) (e.g., up to 50% of the oil phase). The emulsions used for the stability experiments were prepared according to Table 13:

TABLE 13

| Water Phase (Phase A) | |
|---|---|
| Aqua | Up to 100.00% w/w |
| Glycerin | 5% w/w |
| MgSO$_4$ | 2% w/w |
| EDTA | 0.05% w/w |
| Phenoxyethanol and Parabens | 0.5% w/w |
| Oil Phase (Phase B) | |
| Isodecyl Neopentanoate | 6% w/w |
| Paraffinum liquidum | 4% w/w |
| Cyclopentasiloxane, Cyclohexasiloxane | 15% w/w |
| Emulsifier* | 5% w/w |

*Tested emulsifiers: Emulsifier P2, emulsifier P3, emulsifier P4, emulsifier P6, and emulsifier P10 (each prepared as described in Example 2). Glycerin was used as a humectant; MgSO$_4$ was used as a stabilizer; EDTA was used as a chelating agent; phenoxyethanol and parabens were added as preservatives; isodecyl neopentanoate and paraffinum liquidum were used as oil phase emollients; and cyclopentasiloxane and cyclohexasiloxane were the silicon oils also used as oil phase emollient.

Phase A was added to Phase B at room temperature (25° C.) homogenizing for 5 minutes. In this example both phases were prepared without heating: it was a completely cold process. Stability was evaluated by visual inspection upon incubation of the various emulsions at 50° C. and the results are shown in Table 14:

TABLE 14

| Emulsion | 1 week | 2 weeks | 3 weeks | 1 Month |
|---|---|---|---|---|
| Example 2 Emulsifier P2 | Ok | Ok | Ok | Ok |
| Example 2 Emulsifier P3 | Ok | Ok | Ok | Ok |
| Example 2 Emulsifier P4 | Ok | Ok | Ok | Ok |
| Example 2 Emulsifier P6 | Ok | Ok | Ok | Ok |
| Example 2 Emulsifier P10 | Ok | Ok | Ok | Ok |

Example 10

Silicon Emulsifiers Co-Emulsifying Properties

Emulsifiers prepared as described in Example 2 were tested as in combination with silicon emulsifiers for their ability to stabilize water-in-oil emulsions in presence of silicon oil. The emulsions used for the stability experiments were prepared according to Table 15:

TABLE 15

| Water Phase (Phase A) | |
|---|---|
| Aqua | Up to 100.00% w/w |
| Glycerin | 5% w/w |
| MgSO$_4$ | 2% w/w |
| EDTA | 0.05% w/w |
| Phenoxyethanol and Parabens | 0.5% w/w |
| Oil Phase (Phase B) | |
| Magnesium Stearate | 2% w/w |
| Isodecyl Neopentanoate | 8% w/w |
| Paraffinum liquidum | 5% w/w |
| Cyclopentasiloxane, Cyclohexasiloxane | 10% w/w |
| Silicon Emulsifier** | 3% w/w |
| Emulsifier* | 2% w/w |

*Tested emulsifiers: Emulsifier P2, emulsifier P3, emulsifier P4, emulsifier P6, and emulsifier P10 (each prepared as described in Example 2).
**Silicon emulsifiers: Cetyl PEG/PPG-10/1 Dimethicone; Lauryl PEG-9 Polydimethylsiloxyethyl Dimethicone; and Cyclopentasiloxane (and) PEG/PPG-18/18 Dimethicone. Glycerin was used as a humectant; MgSO$_4$ was used as a stabilizer; EDTA was used as a chelating agent; phenoxyethanol and parabens were added as preservatives; magnesium stearate was used as rheological modifier/thickener; isodecyl neopentanoate, paraffinum liquidum, cyclopentasiloxane and cyclohexasiloxane were used as oil phase emollients; the last two being silicon oils.

Phase A was added to Phase B at room temperature (25° C.) homogenizing for 5 minutes. In this example both phases were prepared without heating: it was a completely cold process. Stability was evaluated by visual inspection upon incubation of the various emulsions at 50° C. and the results are shown in Table 16:

TABLE 16

| | Emulsion | | | | |
|---|---|---|---|---|---|
| Silicon Emulsifier | Emulsifier | 1 week | 2 weeks | 3 weeks | 1 Month |
| Cetyl PEG/PPG-10/1 Dimethicone | / | Ok | Ok | Ok | Emulsion breaks |
| | Example 2 Emulsifier P2 | Ok | Ok | Ok | Ok |
| | Example 2 Emulsifier P3 | Ok | Ok | Ok | Ok |
| | Example 2 Emulsifier P4 | Ok | Ok | Ok | Ok |
| | Example 2 Emulsifier P6 | Ok | Ok | Ok | Ok |
| | Example 2 Emulsifier P10 | Ok | Ok | Ok | Ok |
| Lauryl PEG-9 Polydimethylsiloxyethyl Dimethicone | / | Ok | Ok | Ok | Emulsion breaks |
| | Example 2 Emulsifier P2 | Ok | Ok | Ok | Ok |
| | Example 2 Emulsifier P3 | Ok | Ok | Ok | Ok |
| | Example 2 Emulsifier P4 | Ok | Ok | Ok | Ok |
| | Example 2 Emulsifier P6 | Ok | Ok | Ok | Ok |
| | Example 2 Emulsifier P10 | Ok | Ok | Ok | Ok |

TABLE 16-continued

| Emulsion | | | | | |
|---|---|---|---|---|---|
| Silicon Emulsifier | Emulsifier | 1 week | 2 weeks | 3 weeks | 1 Month |
| Cyclopentasiloxane (and) PEG/PPG-18/18 Dimethicone | / | Ok | Ok | Ok | Emulsion breaks |
| | Example 2 Emulsifier P2 | Ok | Ok | Ok | Ok |
| | Example 2 Emulsifier P3 | Ok | Ok | Ok | Ok |
| | Example 2 Emulsifier P4 | Ok | Ok | Ok | Ok |
| | Example 2 Emulsifier P6 | Ok | Ok | Ok | Ok |
| | Example 2 Emulsifier P10 | Ok | Ok | Ok | Ok |

The results presented in Examples 9 and 10 show that the emulsifiers according to Example 2 are suitable to produce stable w/o emulsions in the presence of a high amount of silicon oil, and may be used in association with silicon emulsifiers to generate emulsions that are more stable than corresponding emulsions comprising the silicon emulsifiers alone.

Example 11

Preparation of Paraffin Oil-Free Emulsions Using Example 2 Emulsifiers

In general, paraffins have a positive influence on emulsion stability. The results presented below show that it is possible to produce stable W/O emulsions which do not require any paraffins to achieve useful stability.

TABLE 17

| Water Phase (Phase A) | |
|---|---|
| Aqua | Up to 100.00% w/w |
| Glycerin | 5% w/w |
| MgSO$_4$ | 1% w/w |
| Propylene Glycol | 3% w/w |
| Phenoxyethanol and Parabens | 0.5% w/w |
| Oil Phase (Phase B) | |
| Zinc Stearate | 1.5% w/w |
| *Persea Gratissima* Oil | 2.5% w/w |
| Dicaprylyl Ether | 8.5% w/w |
| Dicaprylyl Carbonate | 8.5% w/w |
| *Butyrospermum Parkii* (Shea Butter) | 0.5% w/w |
| *Euphorbia Cerifera* (candelilla) wax | 2% w/w |
| Emulsifier* | 4.5% w/w |

*Tested emulsifiers: Emulsifier P2, emulsifier P3, emulsifier P4, emulsifier P6, and emulsifier P10 (each prepared as described in Example 2). Glycerin was used as a humectant; MgSO$_4$ was used as a stabilizer; propylene glycol was used as humectant; phenoxyethanol and parabens were added as preservatives; zinc stearate was used as rheological modifier/thickener; *Persea Gratissima* Oil, dicaprylyl ether, dicaprylyl carbonate, *Butyrospermum Parkii* (shea butter) and *Euphorbia Cerifera* (candelilla) wax were used as oil phase emollients.

The water (Phase A) and oil (Phase B) phases were heated at about 75° C., then Phase B was added to Phase A and homogenized for 5 minutes. The mixture was cooled under gentle stirring and emulsion stability was evaluated by visual inspection upon incubation of the various emulsions at 50° C. The results are shown in Table 18.

TABLE 18

| Emulsions | 1 week | 2 weeks | 3 weeks | 1 Month |
|---|---|---|---|---|
| Example 2 Emulsifier P2 | Ok | Ok | Ok | Ok |
| Example 2 Emulsifier P3 | Ok | Ok | Ok | Ok |
| Example 2 Emulsifier P4 | Ok | Ok | Ok | Ok |
| Example 2 Emulsifier P6 | Ok | Ok | Ok | Ok |
| Example 2 Emulsifier P10 | Ok | Ok | Ok | Ok |

Example 12

Freeze-Thaw Stability of Emulsions Prepared Using Example 2 Emulsifiers

Freeze-thaw cycle testing is a part of stability testing that allows determining if a formula will remain stable under various conditions. Freeze-thaw testing is conducted by exposing the product to freezing temperatures (approximately −15° C.) for 24 hours, then allowing to thaw at room temperature for 24 hours. This completes one cycle. W/O emulsions obtained with emulsifiers of the present invention and described in Table 19 below are stable up to 5 freeze-thaw cycles as shown in Table 20 below.

TABLE 19

| Water Phase (Phase A) | |
|---|---|
| Aqua | Up to 100.00% w/w |
| Glycerin | 5% w/w |
| MgSO$_4$ | 2% w/w |
| EDTA | 0.05% w/w |
| Phenoxyethanol and Parabens | 0.5% w/w |
| Oil Phase (Phase B) | |
| Magnesium Stearate | 2% w/w |
| Isodecyl Neopentanoate | 5% w/w |
| Paraffinum liquidum | 3% w/w |
| Cyclopentasiloxane, Cyclohexasiloxane | 15% w/w |
| Emulsifier* | 5% w/w |

*Tested emulsifiers: Emulsifier P2, emulsifier P3, emulsifier P4, emulsifier P6, and emulsifier P10 (each prepared as described in Example 2). Glycerin was used as a humectant; MgSO$_4$ was used as a stabilizer; EDTA was used as a chelating agent; phenoxyethanol and parabens were added as preservatives; magnesium stearate was used as rheological modifier/thickener; isodecyl neopentanoate, paraffinum liquidum, cyclopentasiloxane and cyclohexasiloxane were used as oil phase emollients.

Phase A was added to Phase B at room temperature (25° C.) homogenizing for 5 minutes. In this example both phases were prepared without heating: it was a completely cold process. Stability was evaluated by visual inspection as described above and the results are shown in Table 20:

TABLE 20

| Emulsions | 1 cycle | 2 cycles | 3 cycles | 4 cycles | 5 cycles |
|---|---|---|---|---|---|
| Example 2 Emulsifier P2 | Ok | Ok | Ok | Ok | Ok |
| Example 2 Emulsifier P3 | Ok | Ok | Ok | Ok | Ok |
| Example 2 Emulsifier P4 | Ok | Ok | Ok | Ok | Ok |
| Example 2 Emulsifier P6 | Ok | Ok | Ok | Ok | Ok |
| Example 2 Emulsifier P10 | Ok | Ok | Ok | Ok | Ok |

Example 13

Sun Protection W/O Emulsions

Emulsifiers prepared as described in Example 2 were used in sun protection formulations. These formulations were prepared according to Table 21.

TABLE 21

| Water Phase (Phase A) | |
|---|---|
| Aqua | Up to 100.00% w/w |
| Glycerin | 5% w/w |
| NaCl | 2% w/w |
| EDTA | 0.05% w/w |
| Phenoxyethanol and Parabens | 0.5% w/w |
| Zinc Oxide | 4% w/w |
| Oil Phase (Phase B) | |
| Magnesium Stearate | 2% w/w |
| Isodecyl Neopentanoate | 3% w/w |
| Paraffinum liquidum | 3% w/w |
| Cyclopentasiloxane, Cyclohexasiloxane | 9% w/w |
| Emulsifier* | 4% w/w |
| Ethylhexyl Methoxycinnamate | 7% w/w |
| Ethylhexyl Salicylate | 5% w/w |
| Titanium Dioxide (and) Trimethoxycaprylylsilane | 4% w/w |

*Tested emulsifiers: Emulsifier P2, emulsifier P3, emulsifier P4, emulsifier P6, and emulsifier P10 (each prepared as described in Example 2). Glycerin was used as a humectant; NaCl was used as emulsion stabilizer EDTA was used as a chelating agent; phenoxyethanol and parabens were added as preservatives; zinc oxide, titanium dioxide (and) trimethoxycaprylylsilane, ethylhexyl methoxycinnamate and ethylhexyl salicylate were used as sunblocking agents; magnesium stearate was used as rheological modifier/thickener; isodecyl neopentanoate, paraffinum liquidum, cyclopentasiloxane and cyclohexasiloxane were used as oil phase emollients.

Phase A was added to Phase B at room temperature (25° C.-30° C.) homogenizing for 5 minutes. Phase C was added to the A+B mixture and the final mixture was stirred a few minutes. Stability of each formulation was evaluated by visual inspection upon incubation of the various emulsions at 50° C. and the results are shown in Table 22.

TABLE 22

| Emulsions | 1 week | 2 weeks | 3 weeks | 1 Month |
|---|---|---|---|---|
| Example 2 Emulsifier P2 | Ok | Ok | Ok | Ok |
| Example 2 Emulsifier P3 | Ok | Ok | Ok | Ok |
| Example 2 Emulsifier P4 | Ok | Ok | Ok | Ok |
| Example 2 Emulsifier P6 | Ok | Ok | Ok | Ok |
| Example 2 Emulsifier P10 | Ok | Ok | Ok | Ok |

Although the present invention has been described hereinabove by way of specific embodiments thereof, it can be modified, without departing from the spirit and nature of the subject invention as defined in the appended claims.

The invention claimed is:

1. A water-in-oil (W/O)-stabilizing emulsifier comprising:
   (a) polyglycerol fatty acid esters consisting of saturated and unsaturated fatty acid esters of polyglycerol;
   (b) polyhydroxystearic acid copolymers consisting of copolymers of hydroxystearic acid with saturated and unsaturated fatty acids; and
   (c) hydroxystearic acid.

2. The emulsifier of claim 1, wherein (a) consists of mono-substituted or mono-esterified polyglycerol fatty acid esters.

3. The emulsifier of claim 1, wherein (b) consists of copolymers of 12-hydroxystearic acid with saturated and unsaturated fatty acids.

4. The emulsifier of claim 3, wherein (b) consists of copolymers of about 0.5 to 0.8 equivalents of 12-hydroxystearic acid with about 1 equivalent of saturated and unsaturated fatty acids.

5. The emulsifier of claim 3, wherein (b) has an acid value of between about 145 mg KOH/g and about 165 mg KOH/g.

6. The emulsifier of claim 1, wherein (c) consists of 12-hydroxystearic acid.

7. The emulsifier of claim 1, wherein (a), (b), or both (a) and (b) are produced from a mixture of saturated and unsaturated fatty acids comprising:
   (i) 10-20% w/w palmitic acid (C16);
   (ii) 0.2-5% w/w palmitoleic acid (C16:1);
   (iii) 10-20% w/w stearic acid (C18);
   (iv) 40-60% w/w oleic acid (C18:1);
   (v) 10-20% w/w linoleic acid (C18:2); and
   (vi) 0.3-5% w/w linolenic acid (C18:3).

8. The emulsifier of claim 7, wherein said mixture of saturated and unsaturated fatty acids is from: almond oil, olive oil, coconut oil, cocoa tree oil, soybean oil, palm oil, sunflower oil, or any combination thereof.

9. The emulsifier of claim 1, wherein (a), (b) and/or (c) are obtained from vegetable sources.

10. The emulsifier of claim 1, wherein said emulsifier has a melting point suitable for cold-process emulsions, and wherein said melting point is (i) below about 48, 47, 46, 45, 44, 43, 42, 41, 40, 39, 38, 37, 36, 35, 34, 33, 32, 31, 30, 29, 28, 27, 26, 25, 24, 23, 22, or 21° C.; or (ii) between about 19° C. and about 48° C.

11. The emulsifier of claim 1, wherein said emulsifier comprises:
   (a) about 35-52% w/w of said polyglycerol fatty acid esters;
   (b) about 40-65% w/w of said polyhydroxystearic acid copolymers; and
   (c) about 0.5-6% w/w of said hydroxystearic acid.

12. The emulsifier of claim 1, (i) having a viscosity of between about 3000 cP to about 110,000 cP at 25° C.; and/or (ii) which is homogenous at room temperature.

13. The emulsifier of claim 1, wherein said emulsifier enables stabilization of a W/O emulsion comprising (i) up to 90%, up to 91%, up to 92%, up to 93%, or up to 94% w/w water for at least 1 month at 50° C.; or (ii) a polar oil.

14. A composition comprising a water-in-oil (W/O) emulsion stabilized by the emulsifier as defined in claim 1.

15. The composition of claim 14, further comprising (i) a thermolabile active ingredient; (ii) an emollient; (iii) a thickener or rheological modifier; or (iv) a combination of at least two of (i) to (iii).

16. The composition of claim 14, wherein said composition comprises up to 90%, up to 91%, up to 92%, up to 93%, or up to 94% w/w water.

17. The composition of claim 14, wherein said W/O emulsion is stable for at least 1 month at 50° C.

18. The composition of claim 14, which is (i) a cosmetic or a pharmaceutical composition; (ii) a dermatological composition; (iii) a liquid, cream, gel, or wax; or (iv) a combination of at least two of (i) to (iii).

19. The composition of claim 14, wherein said composition further comprises silicon oil.

20. The composition of claim 14, wherein said composition (i) further comprises a silicon emulsifier; (ii) is free of paraffin; or (iii) a combination of (i) and (ii).

21. A method for producing the W/O-stabilizing emulsifier of claim 1, said method comprising mixing:
(a) saturated and unsaturated fatty acid esters of polyglycerol produced by esterifying a mixture of saturated and unsaturated fatty acids with polyglycerol;
(b) copolymers of hydroxystearic acid with saturated and unsaturated fatty acids produced by esterifying a mixture of saturated and unsaturated fatty acids with hydroxystearic acid; and
(c) hydroxystearic acid,
thereby producing said W/O-stabilizing emulsifier.

22. The method of claim 21, wherein (a) consists of mono-substituted or mono-esterified polyglycerol fatty acid esters.

23. The method of claim 21, wherein (a) is produced by esterifying a mixture of saturated and unsaturated fatty acids with polyglycerol-n, wherein n is an integer from 2 to 10.

24. The method of claim 21, wherein (b) is produced by esterifying a mixture of saturated and unsaturated fatty acids with 12-hydroxystearic acid, until an acid value of between about 145 mg KOH/g and about 165 mg KOH/g is reached.

25. The method of claim 21, wherein (c) is 12-hydroxystrearic acid.

26. The method of claim 21, wherein (a), (b), or both (a) and (b) are produced from a mixture of saturated and unsaturated fatty acids comprising:
(i) 10-20% w/w palmitic acid (C16);
(ii) 0.2-5% w/w palmitoleic acid (C16:1);
(iii) 10-20% w/w stearic acid (C18);
(iv) 40-60% w/w oleic acid (C18:1);
(v) 10-20% w/w linoleic acid (C18:2); and
(vi) 0.3-5% w/w linolenic acid (C18:3).

27. The method of claim 26, wherein said mixture of saturated and unsaturated fatty acids is from: almond oil, olive oil, coconut oil, cocoa tree oil, soybean oil, palm oil, sunflower oil, or any combination thereof.

28. The method of claim 21, wherein (a), (b) and/or (c) are obtained from vegetable sources.

29. The method of claim 21, wherein said emulsifier has a melting point suitable for cold-process emulsions, and wherein said melting point is (i) below about 48, 47, 46, 45, 44, 43, 42, 41, 40, 39, 38, 37, 36, 35, 34, 33, 32, 31, 30, 29, 28, 27, 26, 25, 24, 23, 22, or 21° C.; or (ii) between about 19° C. and about 48° C.

30. The method of claim 21, wherein about 35-52% w/w of (a), about 40-65% w/w of (b), and about 0.5-6% w/w of (c) are mixed.

31. The method of claim 21, wherein said emulsifier is produced by melting (a) at about 70 to about 110° C.; mixing with (c); mixing with (b) until dissolution is obtained; and cooling to a temperature between about 50 to about 70° C.

32. The method of claim 21, wherein relative amounts of (a), (b), and (c) are adjusted to produce emulsifiers having viscosity levels between about 3000 cP to about 110,000 cP at 25° C.

33. The method of claim 21, wherein (a), (b), and (c) are mixed to produce an emulsifier that is homogenous at room temperature.

34. The method of claim 21, wherein said emulsifier enables stabilization of a W/O emulsion comprising up to 90% w/w water for at least 1 month at 50° C.

35. A method for producing a water-in-oil (W/O) emulsion, said method comprising mixing a W/O-stabilizing emulsifier comprising: (a) polyglycerol fatty acid esters consisting of saturated and unsaturated fatty acid esters of polyglycerol; (b) polyhydroxystearic acid copolymers consisting of copolymers of hydroxystearic acid with saturated and unsaturated fatty acids; and (c) hydroxystearic acid, or produced by the method defined in claim 21, with an oil phase and an aqueous phase.

36. The method of claim 35, wherein said method is carried out without a heating step.

37. The method of claim 35, wherein said method is carried out at a temperature (i) below about 40° C., below about 35° C., below about 30° C., or below about 25° C.; or (ii) between about 10° C. to about 40° C., between about 15° C. to about 35° C., between about 15° C. to about 30° C., between about 15° C. to about 25° C., or between about 20° C. to about 25° C.

38. The method of claim 35, further comprising adding a thermolabile active ingredient to said emulsion.

39. The emulsifier of claim 1, wherein (a) consists of saturated and unsaturated fatty acid esters of polyglycerol-n, wherein n is an integer from 2 to 10.

40. The emulsifier of claim 1, wherein (a) consists of saturated and unsaturated fatty acid esters of polyglycerol-n, wherein n is 2.

41. The emulsifier of claim 3, wherein (b) consists of copolymers of about 0.6 equivalents of 12-hydroxystearic acid with about 1 equivalent of saturated and unsaturated fatty acids.

42. The emulsifier of claim 3, wherein (b) has an acid value of about 155 mg KOH/g.

43. The composition of claim 19, wherein said silicon oil comprises a cyclosiloxane.

* * * * *